US006234979B1

(12) United States Patent
Merzenich

(10) Patent No.: US 6,234,979 B1
(45) Date of Patent: May 22, 2001

(54) COMPUTERIZED METHOD AND DEVICE FOR REMEDIATING EXAGGERATED SENSORY RESPONSE IN AN INDIVIDUAL WITH AN IMPAIRED SENSORY MODALITY

(75) Inventor: Michael M. Merzenich, San Francisco, CA (US)

(73) Assignee: Scientific Learning Corporation, Berkeley, CA (US)

( * ) Notice: Subject to any disclaimer, the term of this patent is extended or adjusted under 35 U.S.C. 154(b) by 0 days.

(21) Appl. No.: 09/052,741

(22) Filed: Mar. 31, 1998

(51) Int. Cl.[7] ................................................. A61B 10/00

(52) U.S. Cl. ............................................................ 600/559

(58) Field of Search ................................ 600/558, 559, 600/587

(56) References Cited

U.S. PATENT DOCUMENTS

| | | | |
|---|---|---|---|
| 3,855,998 | * 12/1974 | Hidalgo-Briceno | 600/558 |
| 4,158,920 | * 6/1979 | Walker | 600/558 |
| 4,759,070 | 7/1988 | Voroba et al. | 381/60 |
| 5,024,235 | 6/1991 | Ayers | 128/732 |
| 5,092,835 | 3/1992 | Schurig et al. | 600/9 |
| 5,387,104 | 2/1995 | Corder | 434/156 |
| 5,724,987 | 3/1998 | Gevins et al. | 128/731 |
| 6,019,607 | 2/2000 | Jenkins et al. | 434/116 |

FOREIGN PATENT DOCUMENTS

| | | | |
|---|---|---|---|
| 4431493A1 | 3/1996 | (DE) | A61F/11/06 |
| 2134689A | 8/1984 | (GB) . | |

OTHER PUBLICATIONS

"Hearing Equals Behavior", Guy Berard, 1993.*
Merzenich, et al., "Temporal Processing Deficits of Language–Learning Impaired Children Ameliorated by Training," *Science*, vol. 271, pp. 77–81 (1996).

* cited by examiner

Primary Examiner—Max Hindenburg
(74) Attorney, Agent, or Firm—Beyer Weaver & Thomas, LLP

(57) ABSTRACT

The present invention provides a method and apparatus for implementing a training regimen which alleviates exaggerated sensory, perceptual, cognitive and/or emotional response problems. For example, in the aural domain, some autistic individuals are hypersensitive to one of the senses, e.g., sound. As discussed above, sounds at the specific frequency can cause discomfort to these autistic individuals even when presented at an intensity level which normally is not perceived as being too loud by most individuals. Similarly, tinnitus afflicted individuals also suffer from disconcerting perceived ringing sensations in their ears. The present invention hypothesizes that a catastrophic cascade of responses within a "supergroup" of auditory neurons is triggered by a hypersensitive response to a particular frequency or range of frequencies. The self sustaining cascade is very much like an epileptic seizure in which the sudden involuntary response of a relatively small group of neurons trigger responses in a supergroup of neurons located in the motor control region of the brain. In accordance with the present invention, the abnormally sensitive response problem associated with supergroups can be substantially alleviated via a remedial training regimen which emphasizes the redevelopment of the afflicted individual's ability to make fine sensory distinctions and/or the improvement of the individual's differential sensory acuteness. Providing the regimen to the individual consistently over a period of time increases the likelihood of normal or near normal sensory ability returning.

6 Claims, 3 Drawing Sheets

COMPUTERIZED METHOD AND DEVICE FOR REMEDIATING EXAGGERATED SENSORY RESPONSE IN AN INDIVIDUAL WITH AN IMPAIRED SENSORY MODALITY

BACKGROUND OF THE INVENTION

1. Field of the Invention

The present invention relates to alleviation of abnormal response problems. More particularly, the present invention relates to a computerized method for the remediation of exaggerated responses, such as in sensory, perceptual, cognitive and/or emotional domains of an individual.

2. Description of the Related Art

Some integrated such as sensory, perceptual, cognitive and/or emotional response problems in individuals are associated with neural dysfunction. Examples include autism, epilepsy, dyslexia, PDD, attention deficit disorder (ADD) including ADD with hyperactivity disorder (ADD/HD), focal dystonias and obsessive/compulsive disorders (OCD).

For example, in some autistic individuals, an exaggerated integrated sensory response problem manifests itself as a hypersensitivity to a specific audible frequency (or frequencies). Sounds at the specific frequency can cause discomfort to these autistic individuals even when presented at a sound level not perceived as being too loud by most individuals. Unfortunately these frequencies belong within the frequency spectrum of normal speech. As a result, these autistic individuals consciously avoid exposure to the "painful" sounds. In the case of a young autistic child, the conscious avoidance of "painful" sounds greatly impedes the child's development of spoken language skills, and hence delays the child's acquisition of social skills.

Guy Berard, a French physician has experimented treating autistic children who are hypersensitive to certain frequencies, e.g., 2000 Hz at 50 decibels. His treatment involved wherein "the tapes were filtered to remove those frequencies which the audiogram indicated were injurious" (Hearing Equals Behavior, by Guy Berard, M.D., published in 1993 by Keats Publishing Inc., 27 Pine Street (Box 876), New Canaan, Conn., see page 81, lines 16–18).

The system alternated low and high sounds in an irregular pattern, so that the patient does not become accustomed to the rhythm. Filters attenuated the traumatizing frequencies, while the intensity is determined by the original source. As the sounds are produced, they are modified; higher, lower, louder, softer, filtered, unfiltered. They are controlled in such a way that cannot affect the patient traumatically, no matter what hearing problem he presents. (Page 81, last line to page 82, lines 1–7 in Hearing Equals Behavior by Guy Berard, published in 1993 by Keats Publishing Inc., 27 Pine Street (Box 876), New Canaan, Conn.).

Berard's treatment strategy appears to be based on a controlled introduction of the offensive sound(s) to gradually increase the individual's tolerance to the problematic sounds by using "sounds which are alternately stronger, softer, higher, lower, originating from the left and from the right, . . . [in] a bearable, non[-]aggressive but still therapeutic intensity . . . [with] an appropriate rhythm; alternating the sounds too quickly or too slowly would diminish the effectiveness of the training." (Page 80, lines 20–26 in Hearing Equals Behavior by Guy Berard).

Arguendo, even if the individuals treated by the Berard technique eventually develop tolerance to a problematic frequency, they may not be able to distinguish the problematic frequency against background noise or against other frequencies or differentiate between problematic frequencies. In other words, while the hypersensitivity to a particular problematic frequency may have been partially alleviated, the underlying inability to differentiate frequencies remains untreated, and the individual may continue to integrate the problematic frequency with surrounding frequencies.

Yet another exaggerated aural response problem is tinnitus, in which afflicted individuals perceive a "ringing" sensation in one or both ears. Tinnitus is commonly caused by damage to the inner ear resulting in a permanent loss of sensitivity to a specific frequency or a band of frequencies. The perceived ringing may be triggered by an external sound or may be spontaneous. The duration and amplitude of the ringing sensation can vary widely from individual to individual.

Hypersensitivity can also occur in other senses such as touch, vision and taste. For example, some autistic individuals are hypersensitive to touch. As children, they shy away from hugs and other forms of physical social contact. Again, if untreated, social problems can develop, e.g., the reluctance to shake hands with friends.

Ferrie C. D. et al published in the Journal of Neurology, Neurosurgery and Psychiatry, August 1994, vol. 57(8), pages 925–931, a study involving fifteen cases of seizures occurring while subjects were playing video arcade games. In nine of the fifteen cases, the subjects experienced their first seizure while playing video games. Two thirds of these subjects had idiopathic generalized epilepsy and mainly reported generalized tonic seizures, but some had typical absence seizures and myoclonic jerks while playing video games. 30% with idiopathic generalized epilepsy had juvenile myoclonic epilepsy. Overall, 70% of subjects with idiopathic generalized epilepsy were photosensitive to intermittent photic stimulation and the mechanism of seizure provocation was probably similar to that of television induced seizures, although sensitivity to specific patterns was sometimes important. Two children had self-induced video game seizures.

In this study, non-photic factors such as excitement, fatigue, sleep deprivation, cognitive processing, and diurnal variation in susceptibility seemed to be important seizure precipitants, particularly in non-photo-sensitive patients. 29% of the subjects had partial (mainly occipital) video game associated seizures. Occipital spikes were common in the EEG of these subjects. Photosensitivity to intermittent photic stimulation may have been important in two subjects but in the other subjects, who all played arcade video games, other mechanisms need to be considered. Video game associated seizures are a feature of several epileptic syndromes and differ in precipitants and appropriate management.

In view of the foregoing, there are desired improved techniques for addressing exaggerated response problems, e.g., hypersensitivity, using a training regimen that addresses the root of the sensory, perceptual, cognitive and/or emotional problem and not just the symptoms. Such a regimen should offer a comprehensive solution thereby enabling the affected individuals to develop substantially normal sensory response capabilities in the longer term.

SUMMARY OF THE INVENTION

The present invention provides a method and apparatus for implementing a training regimen which alleviates exaggerated sensory, perceptual, cognitive and/or emotional response problems.

For example, in the aural domain, some autistic individuals are hypersensitive to one of the senses, e.g., sound. As discussed above, sounds at the specific frequency can cause discomfort to these autistic individuals even when presented at an intensity level which normally is not perceived as being too loud by most individuals. These individuals appear to integrate their perception of individual frequencies within a spectrum of otherwise differentiable frequencies. Similarly, tinnitus afflicted individuals also suffer from disconcerting perceived ringing sensations in their ears.

The present invention hypothesizes that a catastrophic cascade of responses within a "supergroup" of auditory neurons is triggered by a hypersensitive response to a particular frequency or range of frequencies. The self sustaining cascade is very much like an epileptic seizure in which the sudden involuntary response of a relatively small group of neurons trigger responses in a supergroup of neurons located in the motor control region of the brain.

Similarly, in the visual domain, some individuals, when engaged in video games in a noisy and dimly lit video arcade environment with lots of loud sounds occurring in association with "bright flashes", e.g., exploding targets, experience the supergroup phenomenon. These loud flashes tend to drive the entire visual system in synchrony (both fovial and peripheral vision) and activate large portions of the retina as well as the auditory system. These large volleys of multi-modal synchronous neural activity can cause multiple supergroup responses in subjects who are hypersensitive in the visual domain and probably in the auditory domain. In such individuals, the multimodal supergroup response can cascade and cause a supergroup response in the motor control neural domain, thereby triggering an epileptic seizure.

The present invention also hypothesizes that while the above described supergroup phenomenon can either be acquired through destructive learning and can be aggravated by postnatal injury. The supergroup trait is often but not necessarily accompanied by a genetic disposition, i.e., the afflicted individuals are born with the trait or propensity for acquiring the supergroup trait. In some afflicted individuals, prenatal injury or prenatal developmental problems are a likely root cause of the supergroup trait, i.e., no destructive learning or postnatal injury has occurred; a good example being the autistic individual.

In accordance with the present invention, the abnormally sensitive response problem associated with supergroups can be substantially alleviated via a remedial training regimen which emphasizes the redevelopment of the afflicted individual's ability to make fine sensory distinctions andlor the improvement of the individual's differential sensory acuteness. Providing the regimen to the individual consistently over a period of time increases the likelihood of normal or near normal sensory ability returning.

In one embodiment of the trainer for remediating exaggerated responses associated a supergroup of neurons in an individual with an associated impaired modality, the trainer includes a stimulator and an input device. The stimulator provides a first stimulus to the individual which substantially corresponds to a first boundary of the supergroup of neurons. The input device receives feedback from the individual indicating the intensity of the individual's response to the first stimulus. In accordance with the invention, a controller, operatively coupled to the stimulator, adaptively modifies the first stimulus based on feedback received from the individual, thereby gradually reducing the sensitivity of the supergroup while avoiding an exaggerated response to the first stimulus.

In another embodiment, the stimulator provides a first and second stimulus which substantially corresponds to a first and second boundary of the supergroup of neurons. The input device receives feedback from the individual indicating the intensity of the individual's response to the first and second stimulus. The controller adaptively modifies the first or second stimulus based on feedback received from the individual, thereby gradually reducing the sensitivity of the supergroup while avoiding an exaggerated response to either the first or second stimulus These and other advantages of the present invention will become apparent upon reading the following detailed descriptions and studying the various figures of the drawings.

DETAILED DESCRIPTION OF THE PREFERRED EMBODIMENTS

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps have not been described in detail in order to not unnecessarily obscure the present invention.

Figure 1:
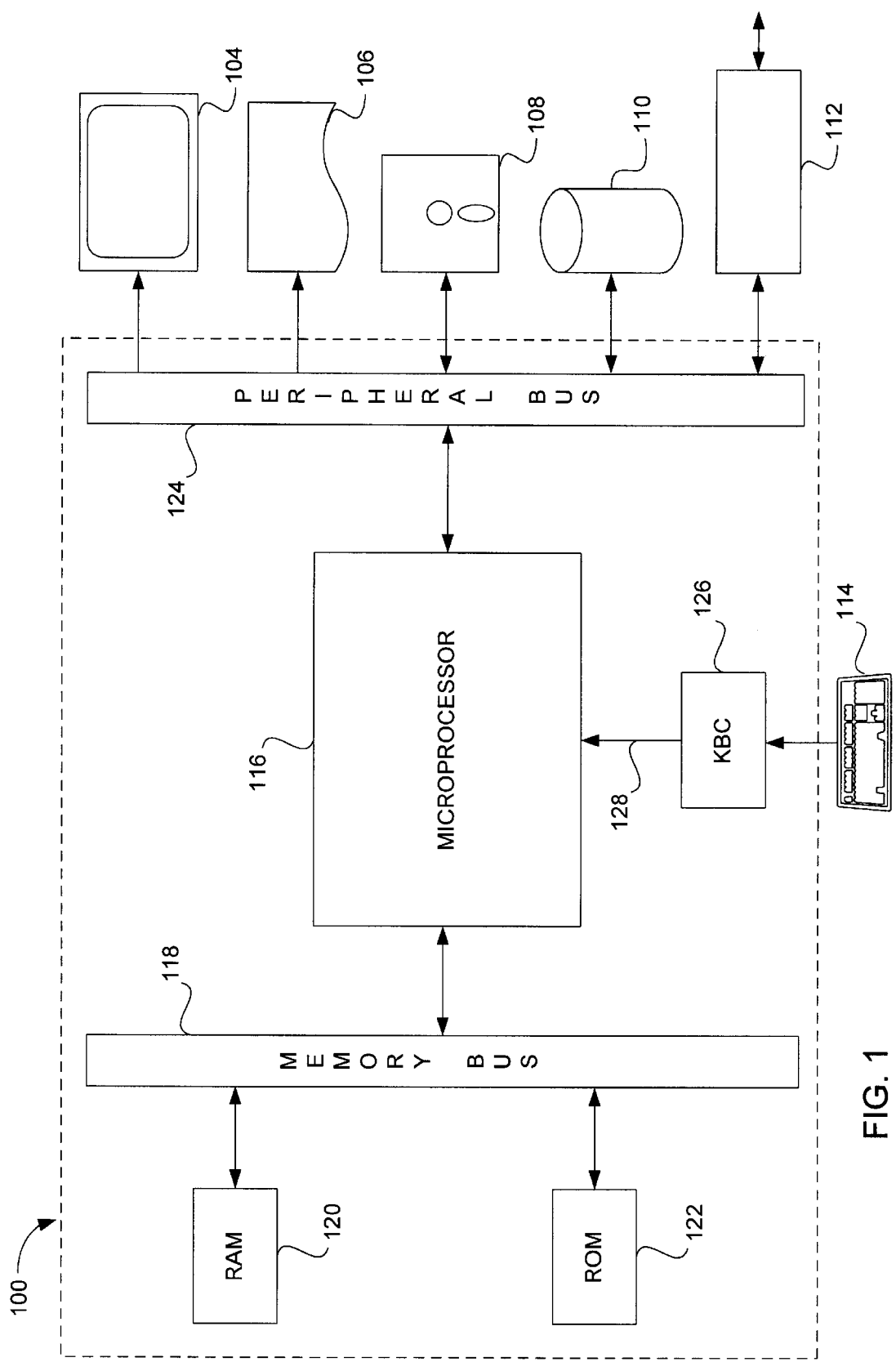
FIG. 1 is a block diagram of an exemplary computer system for practicing the various aspects of the present invention.

FIG. 1 is a block diagram of an exemplary computer system 100 for practicing the various aspects of the present invention. Computer system 100 includes a display screen (or monitor) 104, a printer 106, a floppy disk drive 108, a hard disk drive 110, a network interface 112, and a keyboard 114. Computer system 100 includes a microprocessor 116, a memory bus 118, random access memory (RAM) 120, read only memory (ROM) 122, a peripheral bus 124, and a keyboard controller 126. Computer system 100 can be a personal computer (such as an Apple computer, e.g., an Apple Macintosh, an IBM personal computer, or one of the compatibles thereof), a workstation computer (such as a Sun Microsystems or Hewlett-Packard workstation), or some other type of computer.

Microprocessor 116 is a general purpose digital processor which controls the operation of computer system 100. Microprocessor 116 can be a single-chip processor or can be implemented with multiple components. Using instructions retrieved from memory, microprocessor 116 controls the reception and manipulation of input data and the output and display of data on output devices.

Memory bus 118 is used by microprocessor 116 to access RAM 120 and ROM 122. RAM 120 is used by microprocessor 116 as a general storage area and as scratch-pad memory, and can also be used to store input data and processed data. ROM 122 can be used to store instructions or program code followed by microprocessor 116 as well as other data.

Peripheral bus 124 is used to access the input, output, and storage devices used by computer system 100. In the described embodiment(s), these devices include display screen 104, printer device 106, floppy disk drive 108, hard disk drive 110, and network interface 112. Keyboard controller 126 is used to receive input from keyboard 114 and send decoded symbols for each pressed key to microprocessor 116 over bus 128.

Display screen 104 is an output device that displays images of data provided by microprocessor 116 via peripheral bus 124 or provided by other components in computer system 100. Printer device 106 when operating as a printer provides an image on a sheet of paper or a similar surface. Other output devices such as a plotter, typesetter, etc. can be used in place of, or in addition to, printer device 106.

Floppy disk drive 108 and hard disk drive 110 can be used to store various types of data. Floppy disk drive 108 facilitates transporting such data to other computer systems, and hard disk drive 110 permits fast access to large amounts of stored data.

Microprocessor 116 together with an operating system operate to execute computer code and produce and use data. The computer code and data may reside on RAM 120, ROM 122, or hard disk drive 120. The computer code and data could also reside on a removable program medium and be loaded or installed onto computer system 100 when needed. Removable program mediums include, for example, CD-ROM, PC-CARD, floppy disk and magnetic tape.

Network interface circuit 112 is used to send and receive data over a network connected to other computer systems. An interface card or similar device and appropriate software implemented by microprocessor 116 can be used to connect computer system 100 to an existing network and transfer data according to standard protocols.

Keyboard 114 is used to input commands and other instructions to computer system 100. Other types of user input devices can also be used in conjunction with the present invention. For example, pointing devices such as a computer mouse, a track ball, a stylus, or a tablet can be used to manipulate a pointer on a screen of a general-purpose computer.

The present invention can also be embodied as computer readable code on a computer readable medium. The computer readable medium is any data storage device that can store data which can thereafter be read by a computer system. Examples of the computer readable medium include read-only memory, random-access memory, magnetic data storage devices such as diskettes, and optical data storage devices such as CD-ROMs. The computer readable medium can also be distributed over a network of coupled computer systems so that the computer readable code is stored and executed in a distributed fashion.

The present invention hypothesizes that in some individuals a catastrophic cascade of responses within a "supergroup" of neurons associated with a sensory modality can be triggered by a hypersensitive response to a particular stimulus or range of stimuli. The self sustaining cascade is like an epileptic seizure in which the sudden involuntary response of a relatively small group of neurons trigger responses in a supergroup of neurons located in the motor control region of the brain. Supergroups can also occur in any one of the sensory domains, e.g., hearing, vision, tactile, smell, taste. Hence, it should be possible to train away supergroups associated with an attendable sensory domain.

Although supergroups can occur in individuals without a genetic predisposition, some individuals have brains that are more susceptible to the formation of supergroups. One such susceptible group is autistic individuals who are 30% more prone to having epileptic seizures while the incidence of epileptics in a normal population is less than 5%. Autistic individuals also have a high incidence of hypersensitivity in one or more sensory modalities, e.g., to touch or to sounds, and are highly likely to experience abnormal painful perceptions associated with supergroup formations.

Several studies support the present hypothesis that large assemblies of strongly positively interconnected neurons in the brain, i.e. "supergroups", are created by brain plasticity processes. For example, they can emerge in the brains of autistics in the first 2 to 4 years of life, as is manifested by a hypersensitivity to specific sounds, by strong and sharply coherent neuronal responses evoked specifically by those sounds, and by epileptiform activity during sleep originating in the superior temporal region in which the supergroup has been formed to "represent" those specific sounds. Similar processes give rise to supergroup formation in other forebrain areas, giving rise to a wide variety of sensory-perceptual, motoric and cognitive problems.

In the somatosensory domain, supergroups can be generated in an otherwise completely normal brain by the action of normal brain plasticity mechanisms. For example, they have been created by specific hand uses in which specific hand surfaces have been engaged nearly simultaneously on a heavy, behaviorally attended schedule (Merzenich M M, Recanzone G H, Jenkins W M, How the brain functionally rewires itself. IN: *Natural and Artificial Parallel Computations* M Arbib and J A Robinson eds., MIT Press, New York, 1991; Wang X, Merzenich M M, Sameshima K, Jenkins W M Remodeling of hand representation in adult cortex determined by timing of tactile stimulation. *Nature* 378: 71–75, 1995), as can be achieved by certain experiential uses of the hand. Once created, the strong positive interconnections between coupled brain cells (neurons) that comprise the supergroup are manifested by strong correlations in the response times of its neuronal members, by the generation of a strongly temporally coherent response to applied stimuli, by a broad concurrence of the specific skin surfaces and of the other stimulus parameters that apply for the sensory inputs that resulted in the generation of supergroups, by increased sensitivity to stimulation of those skin surfaces, and by the evocation of relatively strong epileptic-like activity during sleep.

It is also believed that the undesirable effects of supergroups can extend beyond the afflicted individual's waking hours. For example, in a normal individual, during the sleeping hours, the brain, which is in a constant state of reorganization, reinforces its sensory representations in a constructive manner. In contrast, it appears that during the sleeping hours, the brain of an individual afflicted with supergroup experiences a destructive reorganization of its sensory representations.

In the aural domain, some autistic individuals are hypersensitive to sounds at a specific frequency, which can cause discomfort to these autistic individuals, even when presented at an intensity level which is not perceived as being too loud by most individuals. These individuals appear to integrate their representation of individual frequencies within a spectrum of otherwise differentiable frequencies. As a result, a hypersensitive response to a particular frequency or range of frequencies can trigger a catastrophic cascade of responses within the supergroup of neurons associated with the individual's aural modality.

Another aural problem attributable to supergroups is tinnitus. Individuals afflicted with tinnitus perceive a persistent "ringing" of the ear, even in the absence of any external stimuli. The intensity of the ringing perceived by these individuals can range from annoying to actual pain. It is believed that a dominant response within the individual's aural supergroup initiates and sustains the ringing perception.

Aural supergroups also appear to form in the representational remodeling in the cerebral cortex following restricted loss of inputs from the inner ear, in plasticity induced changes that can result in persistent, evoked sounds ("ringing in the ears" or tinnitus; see Robertson D, Irvine D R. Plasticity of frequency organization in auditory cortex of guinea pigs with partial unilateral deafness. J. Comp Neurol 1989282:456–71, 1989; Arnold W, Bartenstein P, Oestreicher E, Romer W, Schwaiger M. Focal metabolic activation in the predominant left auditory cortex in patients suffering from tinnitus: a PET study with [18F]deoxyglucose. J Oto-Rhino-Laryngol 58:195–9, 1996. Lockwood A H, Salvi R J, Coad M L, Towsley M L, Wack D S, Murphy B W. The functional neuroanatomy of tinnitus: evidence for limbic system links and neural plasticity. Neurology 50:114–20, 1996).

In one study involving the visual domain, subjects played video arcade games in a noisy and dimly lit environment with lots of loud sounds occurring in association with "bright flashes", e.g., exploding targets. These loud flashes tend to drive the entire visual system in synchrony (both fovial and peripheral vision) and activate large portions of the retina as well as the auditory system. These large volleys of multimodal synchronous neural activity are capable of triggering multiple supergroup responses in subjects who are hypersensitive in the visual and auditory domains. Such a multimodal supergroup response can cascade into a supergroup response in the motor control neural domain and result in a spontaneous epileptic seizure. In other words, it is possible for one or more supergroups to trigger a cascade response in another supergroup.

The above described supergroup phenomenon can occurs either through destructive learning or injury in individuals born with or without the supergroup trait or propensity for the supergroup trait. For example, in the somatosensory modality, this hypothesis is supported by analysis of before and after MEG brain images of monkeys whose "learned" representation of the tactile sense in the brain has be destructively integrated over time.

Once formed, supergroups can forestall the normal use of the affected brain region. In the examples cited above, the autistic child is unable to make the normal fine distinctions between speech inputs in the range of frequency that applies for the supergroup frequencies, and the child avoids listening to sounds in this frequency range over a critical period in life. Similarly, with supergroup formation involving sensory inputs from the hand to the brain, we have documented that the affected individual ultimately develops a loss of hand movement control.

These supergroups may have other destructive neurological effects due to their abnormally strong impacts neurologically in daily operation or to the strong epileptiform-like activities that they generated during sleeping, or both. For example, in the autistic child, there are many behavioral symptoms of autism that may spring from these abnormal brain regions that are highly active and potentially disorganizing for other activities during both waking and sleeping. With supergroup formation in the hand region, spreading, profound loss of hand control can ultimately result.

Abnormally large and powerful positively-coupled neural cell assemblies can be created by a variety of sensory-perceptual, motor or potentially cognitive activities. In order to form a supergroup in a normal brain, activities should be repetitive and/or very strongly and repetitively rehearsed mentally; activities are stereotyped; input activity patterns are marked by temporally coherent and/or very consistently sequenced events; and external input or mental activities should be consciously attended to. In some individuals with a greater inherited propensity for supergroup formation, for example, in the brains of autistics, these prerequisites can be reduced. Similarly, these prerequisites may be reduced to account for supergroup formation following peripheral loss of input, for example, in the brains of tinnitus sufferers, or in the brains of individuals suffering perceived persistent pain from an amputated limb, i.e. phantom pain.

One explanation for why learned destructive integration can occur is that the brains of most humans are unable to process and hence differentiate sensory input information which is occurring nearly simultaneously, i.e., within tens of milliseconds in time. Eventually, the continued bombardment of these inputs in an attended context begins to destructively retrain the brain. Unable to distinguish these rapidly occurring inputs as temporally distinct inputs, the brain begins to process all the inputs as simultaneous inputs and progressively integrates these inputs over time. Eventually, the individual "trains" his/her brain to integrate these inputs and subsequently, the individual loses the ability to distinguish adjacent inputs. If the degradation occurs in those individuals with a propensity for supergroups, the integration of the inputs further aggravates the existing supergroup problem.

In accordance with the present invention, the hypothesis that supergroups are remediable is supported by the observation that the representation of any sensory modality within the human brain is plastic and is in a constant state of change. Hence, the brain's representation of a sensory modality can be improved by differential stimuli but can also be degraded by integrating stimuli over time. Conversely, an impaired brain representation can also be improved by a differential training regimen. As such, it may be possible to train away or substantially remediate supergroup traits such as abnormal sensory sensitivity in autistic and other language-impaired individuals, tinnitus, some instances of epilepsy, and obsessive compulsive behaviors and other related conditions.

It is believed that by training the brain and improving its ability to make time distinctions or to differentiate between closely spaced bandwidths causes profound changes in the neural interconnections and has the effect of decreasing the likelihood of a supergroup response to previously problematic frequencies. In other words, when the brain acquires the ability to respond selectively to and differentiate narrow frequency bandwidths, there is a corresponding reduction in occurrence of supergroup responses. Intensive training of the brain increases its ability to resolve inputs with higher spectro-temporal resolution results in an increase in the salience of encoded distributed neuronal representations of complex input signals. Hence training results in a neurological representation of the details of complex information in a more powerful form.

Hence, non-invasive training regimens can be used to effectively break down supergroups and substantially reverse the process by which supergroups were formed. This is because by its nature, the supergroup is representing specific, amalgamated input activities with exaggerated power. That amalgamation results in a degraded treatment of input activities in the affected spectral, spatial and temporal domains. Training to break down supergroups can be efficiently achieved by engaging an individual to make fine distinctions that will compete with and progressively re-differentiate the sensory-perceptual abilities in the domain of these amalgamated entities. Accordingly, training should be conducted in a monitored, feedback-controlled and rewarded behavioral context in which the subject is consciously attending to each practice trial in a behavioral training regime. In addition, the training regime should be adaptive, in which the subject makes progressively finer distinctions that progressively create a normal differentiated representation of previously amalgamated input activities.

For a substantial restoration of normal function, the training should actively restore the normal ability to make fine distinctions in the affected spectral andlor spatial and/or temporal domain. In the aural domain, the training should actively restore an ability to resolve the fine features critical for distinguishing features in speech reception for the autistic individual. Similarly, in the tinnitus sufferer, it should re-differentiate the representations of frequencies in the domain of frequency representation of the tinnitus sufferer to improve normal use of that hearing domain for sound localization, speech and sound reception and other hearing tasks. In the somatosensory domain, the training should actively re-differentiate fine sensory and sensory feedback information for guiding fine hand movements in an individual with a supergroup affecting sensory-perceptual representations of hand surfaces or movements.

Initially, individuals are trained to make relatively simple distinctions based on large signal differences that include signals, and spectral, spatial and temporal signal components that fall within the amalgamated supergroup signal representation domain. The individual is then adaptively trained to make progressively finer distinctions until normal discriminative and stimulus recognition capacities are achieved. Stimuli appropriate for restoring high normal functionality are employed in re-training. For example, to train an individual with a manual dysfunction attributable to supergroup formation, development of progressively finer discriminative finger and hand use are incorporated in training.

In one embodiment, training trials are initiated with an observing response that insures that the subject is attending to the task. Feedback for correct performance is provided. Rewards for correct performance and for achieving performance benchmarks are regularly provided. Establishment of normal function for the domain of a supergroup generally requires more than 10 and less than 100 hours of intensive behavioral training using these highly efficient training strategies.

Figure 2:
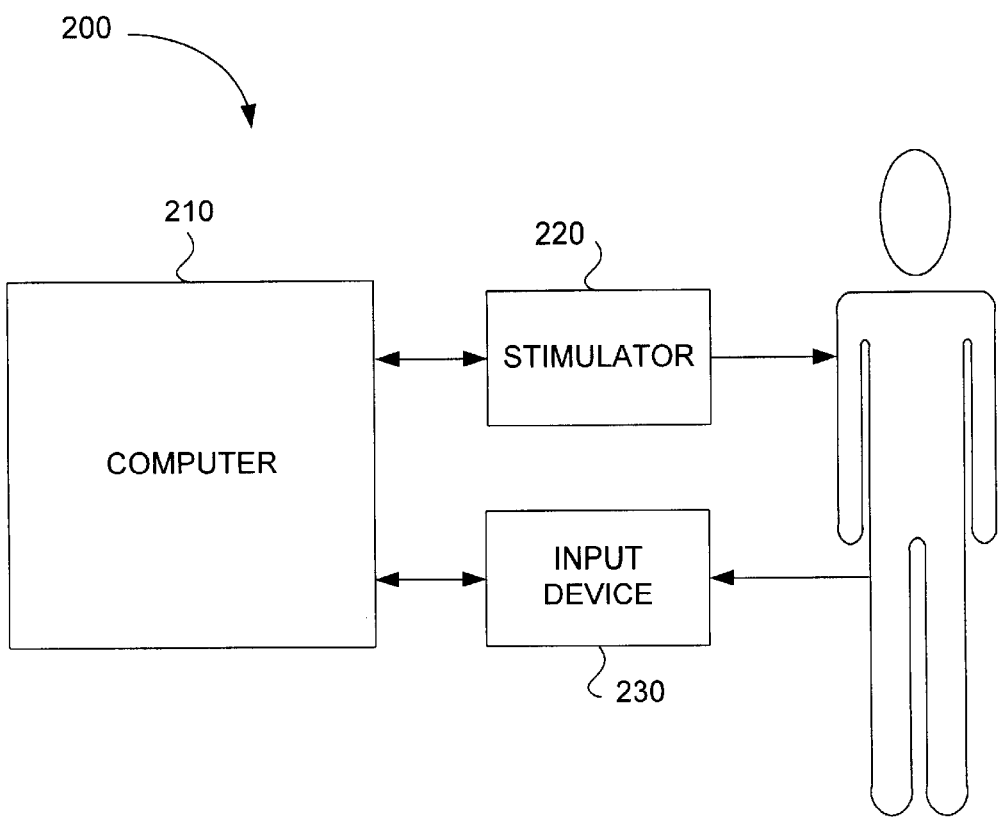
FIG. 2 is a block diagram showing an exemplary hardware environment for practicing the present invention.

Referring now to FIG. 2, a trainer 200 provides an exemplary hardware environment for practicing the various aspects of the present invention. Trainer 200 includes a computer 210 coupled to a stimulator 220 and an input device 230 for providing stimuli to and for receiving feedback from an individual 290, respectively. Computer 210 can be a general purpose computer 100, or an application specific computer system. In this example, the impaired modality is aural. Accordingly, stimulator 220 can be a speaker, a headphone or other suitable means of transmitting aural signals to individual 290. Input device 230 can be keyboard 114, a mouse, a joystick or a microphone.

Figure 3:
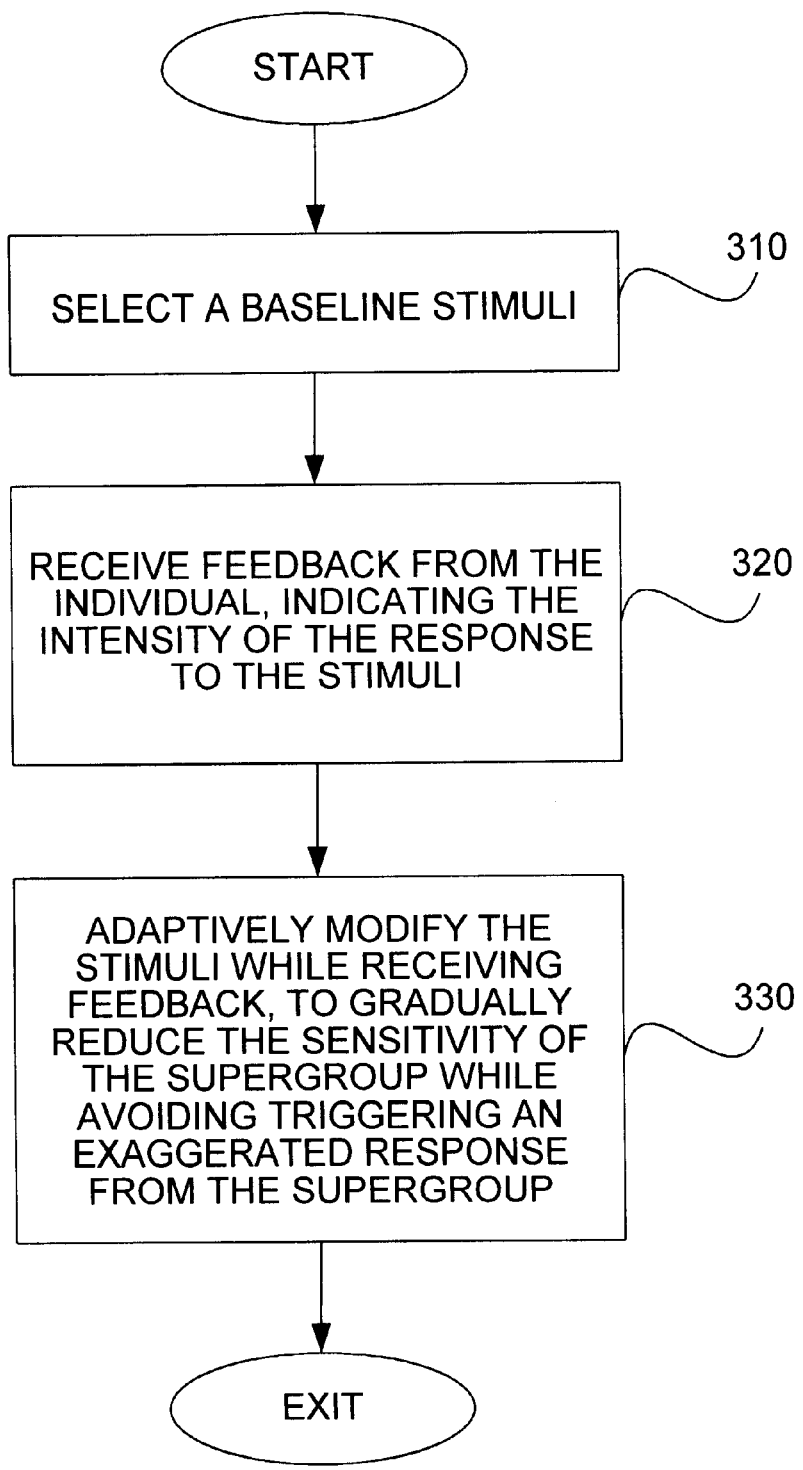
FIG. 3 is a flow chart illustrating the remediation regimen of the present invention.

FIG. 3 is a flowchart illustrating the training regimen of the present invention for remediating a supergroup of neurons of individual 290. In this aural embodiment, training is accomplished by adaptively providing stimuli via stimulator 220. One or more stimulus is selected from a plurality of stimuli corresponding to boundar(ies) of the supergroup of neurons, thereby establishing a stimuli baseline for the training regimen (310). The training regimen adapts to feedback received from individual 290 via input device 230, indicating the intensity of the individual's response to the stimulus (320). Depending on the feedback, the amplitude andlor frequency of the stimulus is modified to gradually increase the difficulty of the training regimen. Hence, the stimuli is adaptively modified to gradually reduce the sensitivity of the supergroup, while avoiding the triggering of an exaggerated supergroup response (330). The difficulty of the training can also be increased by gradually encroaching the boundary of the supergroup. Conversely, where appropriate, the difficulty can be decreased by retreating from the boundary of the supergroup. Depending on the severity of the supergroup problem, the regimen should be include daily sessions over a period of approximately three to ten weeks. The result of this novel training program is an efficient, controlled and progressive breakdown of neuronal supergroups, and a more complete restoration of normal discriminative and usage capabilities.

In one implementation for remediating tinnitus, selected first and second stimulus corresponds to a first and second bordering subgroup from the supergroup of neurons. The rationale for stimulating the bordering subgroups is the belief that by starting at the borders of the supergroup and working inwards into the supergroup, the supergroup response can be gradually diminished. For example, if the subject is hypersensitive to the frequency range 4000 to 6000 Hertz, the selected starting frequency ranges could be 3800–4000 Hertz and 6000–6200 Hertz. Initially, individual 290 is stimulated at these baseline frequency ranges until he/she is able to distinguish both starting frequencies without experiencing a supergroup reaction. One or both stimuli are then modified thereby gradually reducing the difference between the two stimuli, for example at 3900–4100 Hertz and 5000–6100 Hertz.

Many modifications are possible. For example, the present invention can be practiced with or without feedback. Feedback can be manual or automated. Manual feedback can provide an indication that an input is causing discomfort or pain, or the individual is able to distinguish the stimuli. Examples of automated feedback include brain imaging such as MEG and fMRI to monitor changes and responses within the supergroup. Other potentially useful automated feedback indicators include pulse, body temperature, respiratory rate, and blood pressure.

While this invention has been described in terms of several preferred embodiments, there are alterations, permutations, and equivalents which fall within the scope of this invention. For example, while the above-described training regimen addresses a singular uni-modal supergroup, it is possible to remediate multiple supergroups, including cross-modal supergroup(s), either concurrently or consecutively. It is therefore intended that the following appended claims be interpreted as including all such alterations, permutations, and equivalents as fall within the true spirit and scope of the present invention.

What is claimed is:

1. A method of using an apparatus for implementing a training regime having a stimulator and an input device, for remediating exaggerated responses associated with a supergroup of neurons in an individual with an associated with impaired modality, the method comprising:

a) selecting a first stimulus substantially corresponding to a first boundary of the supergroup of neurons;

b) providing said first stimulus using the stimulator;

c) receiving feedback from the individual via the input device indicating the intensity of the individual's response to the first stimulus; and d) adaptively repeating b and c while modifying the first stimulus based on feedback from c, thereby gradually reducing the sensitivity of the supergroup while avoiding an exaggerated response to the first stimulus.

2. The method of claim 1 further comprising:

e) selecting a second stimulus substantially corresponding to a second boundary of the supergroup of neurons;

f) providing said second stimulus using the stimulator;

g) receiving feedback from the individual via the input device indicating the intensity of the individual's response to the second stimulus; and h) adaptively repeating b, c, f and g while modifying the first or second stimulus based on feedback from c and g, thereby gradually reducing the sensitivity of the supergroup while avoiding a substantially exaggerated response to either the first or second stimulus.

3. The method of claim 1 wherein the impaired modality is sensory perceptual based.

4. The method of claim 3 wherein the impaired modality is aural.

5. The method of claim 2 wherein the impaired modality is sensory perceptual based.

6. The method of claim 5 wherein the impaired modality is aural.

* * * * *